(12) United States Patent
Hua et al.

(10) Patent No.: US 11,865,257 B2
(45) Date of Patent: Jan. 9, 2024

(54) ICU-SPECIAL PORTABLE NEBULIZATION DEVICE ENABLING AUTONOMOUS RESPIRATION ACCORDING TO AIRFLOW

(71) Applicant: FEELLIFE HEALTH INC., Guangdong (CN)

(72) Inventors: Jian Hua, Guangdong (CN); Xuefeng Song, Guangdong (CN)

(73) Assignee: FEELLIFE HEALTH INC., Shenzhen (CN)

( * ) Notice: Subject to any disclaimer, the term of this patent is extended or adjusted under 35 U.S.C. 154(b) by 771 days.

(21) Appl. No.: 15/733,521

(22) PCT Filed: Nov. 20, 2018

(86) PCT No.: PCT/CN2018/116509
§ 371 (c)(1),
(2) Date: Aug. 19, 2020

(87) PCT Pub. No.: WO2020/029469
PCT Pub. Date: Feb. 13, 2020

(65) Prior Publication Data
US 2020/0384223 A1   Dec. 10, 2020

(30) Foreign Application Priority Data

Aug. 7, 2018  (CN) .......................... 201810892265.5
Aug. 7, 2018  (CN) .......................... 201821265331.8

(51) Int. Cl.
*A61M 16/08* (2006.01)
*A61M 16/14* (2006.01)
(Continued)

(52) U.S. Cl.
CPC ...... *A61M 16/022* (2017.08); *A61M 16/0666* (2013.01); *A61M 16/0833* (2014.02);
(Continued)

(58) Field of Classification Search
CPC . A61B 17/3474; A61M 11/005; A61M 13/00; A61M 13/003; A61M 15/0085;
(Continued)

(56) References Cited

U.S. PATENT DOCUMENTS

2008/0243050 A1* 10/2008 Power ................ A61B 17/3474
                                                    604/26
2009/0235925 A1*  9/2009 Power ................ B05B 17/0669
                                                    128/200.14
(Continued)

FOREIGN PATENT DOCUMENTS

CN    105722543 A    6/2016
CN    107497026 A   12/2017
CN    107802930 A    3/2018

OTHER PUBLICATIONS

ISA/CN, PCT International Search Report and Written Opinion dated May 14, 2019 issued in PCT International Application No. PCT/CN2018/116509.

*Primary Examiner* — Annette Dixon
(74) *Attorney, Agent, or Firm* — Gottlieb, Rackman & Reisman, P.C.

(57) ABSTRACT

Disclosed is an ICU-special portable nebulization device enabling autonomous respiration according to airflow, which includes a nebulization control host, a nebulization generator provided on the nebulization control host, and a tee connecting pipe provided on the nebulization generator; the nebulization generator comprises a bottom housing, a medicinal solution tank provided on the bottom housing and spaced apart from a space of the bottom housing, a medicinal solution outlet provided on the bottom of the medicinal solution tank, an air guide port provided on the bottom housing at the same side as the medicinal solution outlet, a nozzle tube sheathed on the periphery of the medicinal solution outlet and the air guide port, a partition provided in (Continued)

the nozzle tube which separates the medicinal solution outlet and the air guide port.

11 Claims, 5 Drawing Sheets

(51) Int. Cl.
*A61M 16/00* (2006.01)
*A61M 16/06* (2006.01)
(52) U.S. Cl.
CPC .... *A61M 16/0875* (2013.01); *A61M 16/0883* (2014.02); *A61M 2209/08* (2013.01)
(58) Field of Classification Search
CPC ............ A61M 16/0009; A61M 16/024; A61M 16/0833; A61M 16/1045; A61M 16/1055; A61M 16/107; A61M 16/14; A61M 16/16; A61M 2016/0027; A61M 2016/003; A61M 2016/0039; A61M 2202/0208; A61M 2202/0225; A61M 2202/025; A61M 2202/0266; A61M 2202/0291; A61M 2202/0468; A61M 2202/048; A61M 2205/0294; A61M 2205/33; A61M 2205/3331; A61M 2205/3379; A61M 2205/8206; A61M 2209/084; A61M 2230/04; A61M 2230/205; A61M 2230/50; B05B 12/081; B05B 17/0646; B05B 17/0669; B05B 7/0075; B06B 1/0651; B06B 2201/77
See application file for complete search history.

(56) References Cited

U.S. PATENT DOCUMENTS

| | | | |
|---|---|---|---|
| 2009/0240192 A1* | 9/2009 | Power | B05B 17/0669 604/26 |
| 2011/0178458 A1* | 7/2011 | Power | A61M 13/00 604/24 |
| 2012/0234321 A1* | 9/2012 | Power | B05B 17/0669 128/203.12 |
| 2015/0122248 A1 | 5/2015 | Power et al. | |
| 2022/0379045 A1* | 12/2022 | Baumann | A61M 16/024 |

* cited by examiner

ICU-SPECIAL PORTABLE NEBULIZATION DEVICE ENABLING AUTONOMOUS RESPIRATION ACCORDING TO AIRFLOW

CROSS-REFERENCE TO RELATED APPLICATIONS

This application is a national stage filing under 35 U.S.C. § 371 of international application number PCT/CN2018/116509, filed Nov. 20, 2018, which claims priority to Chinese patent application No. 201810892265.5, filed Aug. 7, 2018 and Chinese patent application No. 201821265331.8, filed Aug. 7, 2018. The contents of these applications are incorporated herein by reference in their entirety.

TECHNICAL FIELD

The present invention relates to the field of medical devices, in particular to an ICU-special portable nebulization device enabling autonomous respiration according to airflow.

BACKGROUND

In the field of modern clinical medicine, the ventilator, as a means of replacing artificial spontaneous ventilation, has been widely used in respiratory failure due to various reasons, anesthesia breathing management during major operations, respiratory support therapy, and emergency resuscitation. Ventilator plays an important role in the field of modern medicine, especially in the ICU ward. The ventilator has the function of providing power to transport air, can replace the work of the human body's own respiratory muscles, and can produce a certain respiratory rhythm, including respiratory frequency and inspiration and expiration ratio. In addition, it can also replace the function of respiratory central nervous system of a human body to control the respiratory rhythm, providing suitable tidal volume (VT) or minute ventilation (MV) to meet the needs of respiratory metabolism. The air supplied by the ventilator is preferably heated and humidified to replace the function of the human nasal cavity, and can supply more $O_2$ than which is contained in the atmosphere to increase the concentration of inhaled $O_2$ and improve oxygenation. The ventilator treatment by nebulization inhalation is an important and effective treatment method among the treatment methods for respiratory system diseases, which uses an atomizer to atomize the medicinal solution into tiny particles for inhalation by a user into the respiratory tract through breathing. The medication is deposited in lungs and is then absorbed through the mucous membrane of lungs, thus achieving the goal of painless, rapid and effective treatment. Therefore, a nebulization treatment device that can effectively cooperate with a ventilator is very important for the patients. However, the existing nebulization device used with the ventilator has the defect that it cannot actively determine the respiratory frequency of the ventilator. The nebulization device usually sprays according to the same frequency as the respiratory frequency of the ventilator that has been set. In addition, there are high operation requirements for users during actual use, and the problem that the nebulization frequency is not synchronized with the respiratory frequency easily occurs, which is very dangerous for the patients.

SUMMARY

In view of the above-mentioned problems, an object of the present invention is to provide an ICU-special portable nebulization device enabling autonomous respiration according to airflow, which actively detects the respiratory state of a ventilator and matches the respiratory frequency, and is simple and convenient to operate.

In order to achieve the above object, the present invention provides an ICU-special portable nebulization device enabling autonomous respiration according to airflow, including: a nebulization control host, a nebulization generator provided on the nebulization control host, and a tee connecting pipe provided on the nebulization generator. The nebulization generator includes a bottom housing, a medicinal solution tank provided on the bottom housing and spaced apart from a space of the bottom housing, a medicinal solution outlet provided on the bottom of the medicinal solution tank, an air guide port provided on the bottom housing at the same side as the medicinal solution outlet, a nozzle tube sheathed on the periphery of the medicinal solution outlet and the air guide port, a partition provided in the nozzle tube which separates the medicinal solution outlet and the air guide port, a nebulization sheet provided between the medicinal solution outlet and the nozzle tube, and a first circuit board provided in the bottom housing which is connected with the nebulization sheet. The partition in the nozzle tube separates the interior of the nozzle tube into a nebulization cavity communicated with the medicinal solution outlet and an air cavity communicated with the air guide port. A sensor connected with the first circuit board is provided in the air cavity. The nozzle tube on the side of the air cavity is provided with a cross-section stopper that blocks the opening of the air cavity. A first ventilation port and a second ventilation port communicated with the air cavity are provided on two sides of the stopper, respectively. The first circuit board extends to the outside of the bottom housing and is connected with the nebulization generator. The nebulization cavity and the air cavity are independent from each other, and the air cavity will not affect the nebulization while detecting the state of the working airflow of the ventilator without affecting at the same time, so that the airflow detection and the nebulization spray do not interfere with each other.

In some embodiments, the nebulization control host includes a housing, a second circuit board provided in the housing, and a button and an indicator light provided on the housing which are connected with the first circuit board.

In some embodiments, the second circuit board includes a main control unit, a power supply circuit connected with the main control unit, and a nebulization driving unit and a battery respectively connected with the power supply circuit. The button and indicator light are respectively connected with the main control unit. The second circuit board is provided with four metal contacts in sequence, which are respectively a detection point A connected with the main control unit, a negative electrode B of the circuit and a nebulization positive electrode C respectively connected with the nebulization driving unit, and a positive electrode D of the power supply connected with the battery. Therefore, the detection point A is connected with the sensor and the main control unit, respectively, and is used to collect signal outputs of the sensor; the negative electrode B of the circuit is connected with the nebulization driving unit, the nebulization sheet and the sensor, respectively, and is shared by the sensor and the nebulization sheet; the positive electrode C of the nebulization is connected with the nebulization driving unit and the nebulization sheet, respectively to provide an alternating voltage required by the nebulization sheet for operation; and the positive electrode D of the power supply is connected with the power supply circuit and the sensor, respectively, to provide a direct voltage required by the sensor for operation.

In some embodiments, the first circuit board is provided with four metal contacts in sequence, which are a first contact conducted with the detection point A, a second contact conducted with the negative electrode B of the circuit, a third contact conducted with the nebulization positive electrode C, and a fourth contact conducted with the positive electrode D of the power supply. The first contact is connected with the sensor, the second contact is connected with the sensor and the nebulization sheet respectively, the third contact is connected with the nebulization sheet, and the fourth contact is connected with the sensor. The main control unit is electrically connected with the sensor, and the nebulization driving unit is connected with the nebulization sheet.

In some embodiments, interfaces are provided on the housing at positions corresponding to the four metal contacts for facilitating conduction of the first circuit board with the metal contacts of the second circuit board after the first circuit board is inserted.

In some embodiments, the power supply circuit includes a DC-AC conversion circuit and a booster circuit; and the nebulization sheet and the sensor use AC voltage and DC voltage, respectively. In addition, the power supply circuit may further include a charging circuit, a power switching circuit, and a rechargeable battery, and is switched to an external power supply when an external AC voltage is connected In some embodiments, the nebulization control host is provided with a clamp for fixing the nebulization control host to the rails of a hospital bed or a table side. The clamp includes a base, an inverted buckle for fixing the nebulization control host on the base, and a movable clip for clamping the whole to the rails of the hospital bed or the table side.

In some embodiments, left and right ends of the tee connecting pipe are respectively provided with a connecting pipe for connecting with an external piping of the ventilator and a face mask. The above connection may be implemented by interference fit connection to make the connection structure simpler. The left and right ends of the tee connecting pipe have different aperture sizes so as to distinguish different ports connecting the ventilator and the face mask. It may be the case that one of the left and right ends of the tee connecting pipe with a larger aperture size is connected with the ventilator, and the other end with a smaller aperture size is connected with the face mask.

In some embodiments, the tee connecting pipe is connected with the nozzle tube. Therefore, a middle port of the tee connecting pipe is connected with the nebulization generator, and the connection thereof may also adopt interference fit connection.

In some embodiments, an inclined bottom surface facing the medicinal solution outlet is provided on the bottom, and an upper cover is provided on the medicinal solution tank.

The present invention has the beneficial effect that it actively detects the respiratory state of the ventilator and matches the respiratory frequency, and is simple and convenient to operate. Since the left and right ends of the tee connecting pipe are respectively provided with the connecting pipe for connecting with the external piping of the ventilator and the face mask, and a middle pipe is communicated with the nebulization generator, the user may ventilate into the pipe. When the ventilator operates, an internal airflow change is detected and judged by the sensor in the air cavity, and then the respiratory state of the ventilator is obtained. When the sensor detects an air flow in the air cavity, the first circuit board sends a signal to the nebulization control host, and then the nebulization control host drives the nebulization driving unit to atomize the medicinal solution for drug delivery to the nebulization sheet in the nozzle tube, so that not only the purpose of combining respiratory therapy with nebulization therapy is achieved, but also the therapeutic effect on the disease is better, avoiding the defect that the nebulization and the respiration are not synchronized. In addition, since the operation requirements on users are low during use, the present invention has the effects of simplicity and convenience. In addition, the nebulization generator and the nebulization control host, as well as their connecting wires can be detachably connected, which is convenient for cleaning and replacing components such as the nebulization generator, and the product can be disassembled, which is convenient to carry, thereby realizing the effect of convenient use.

DETAILED DESCRIPTION

The present invention will be further described in detail below in conjunction with the drawings.

Figure 1:
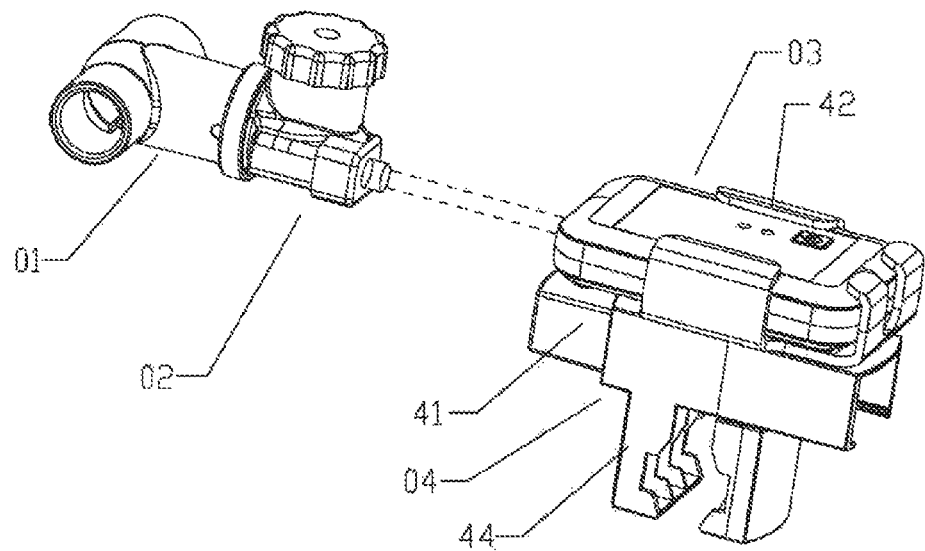
FIG. 1 is a schematic structural diagram of the present invention.
Figure 2:
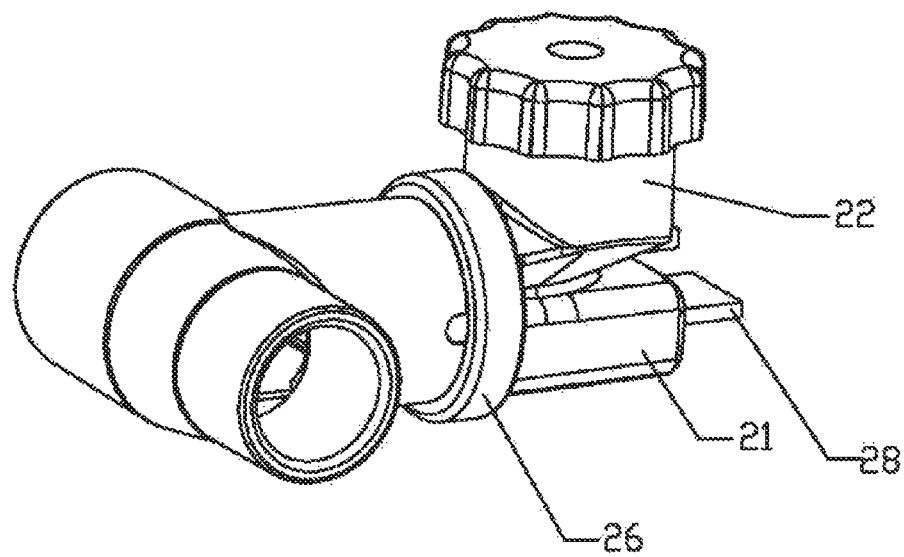
FIG. 2 is a schematic structural diagram of the tee connecting pipe and the nebulization generator after assembly.
Figure 3:
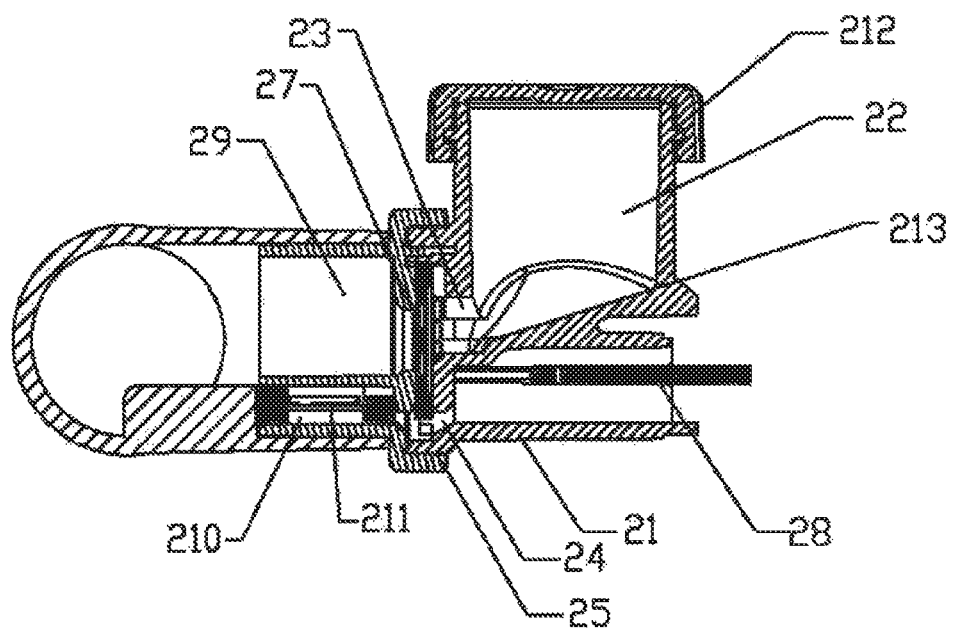
FIG. 3 is a schematic structural diagram of the interior of the tee connecting pipe and the nebulization generator after assembly.
Figure 4:
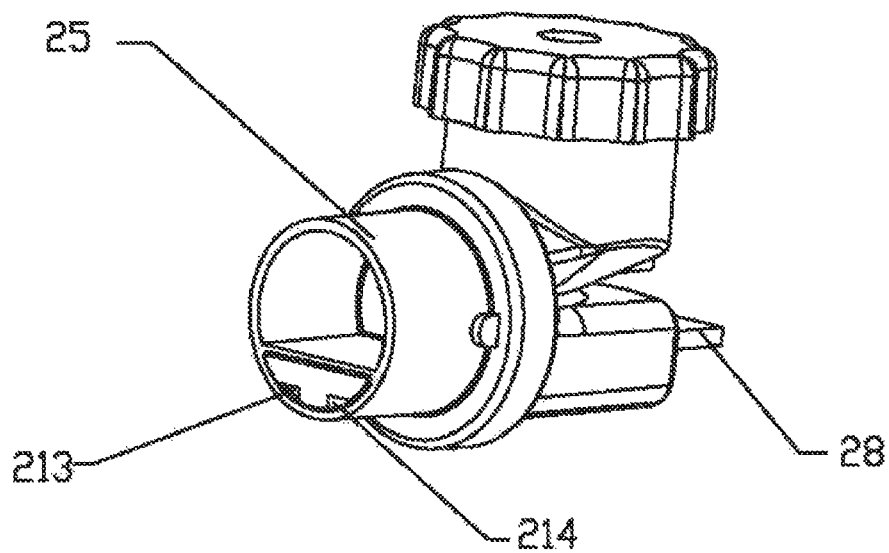
FIG. 4 is a schematic structural diagram of the nebulization generator after assembly.
Figure 5:
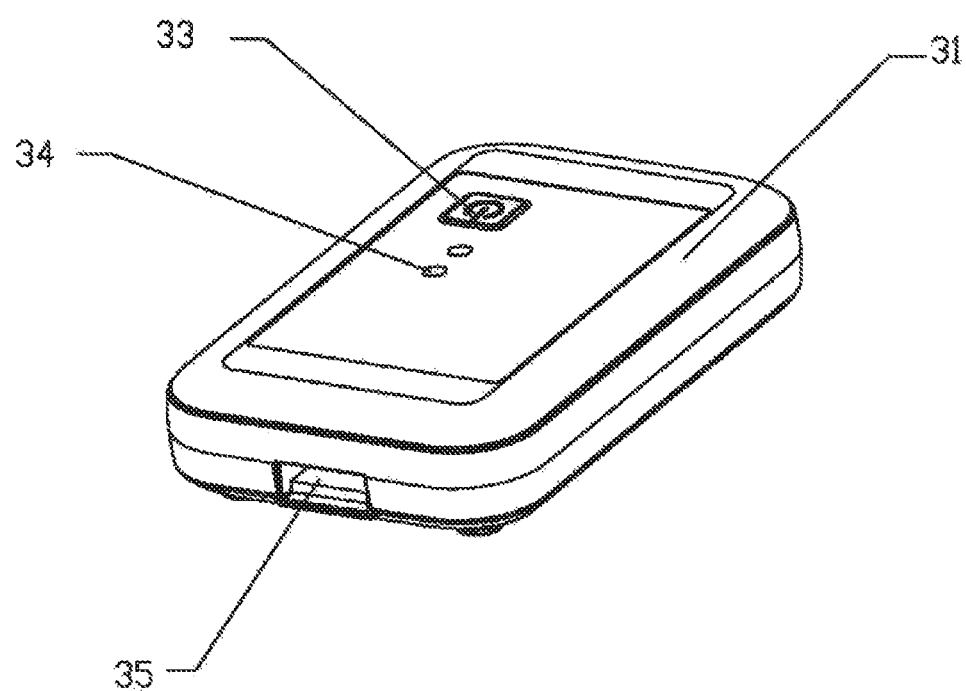
FIG. 5 is a schematic structural diagram of the nebulization control host.
Figure 6:
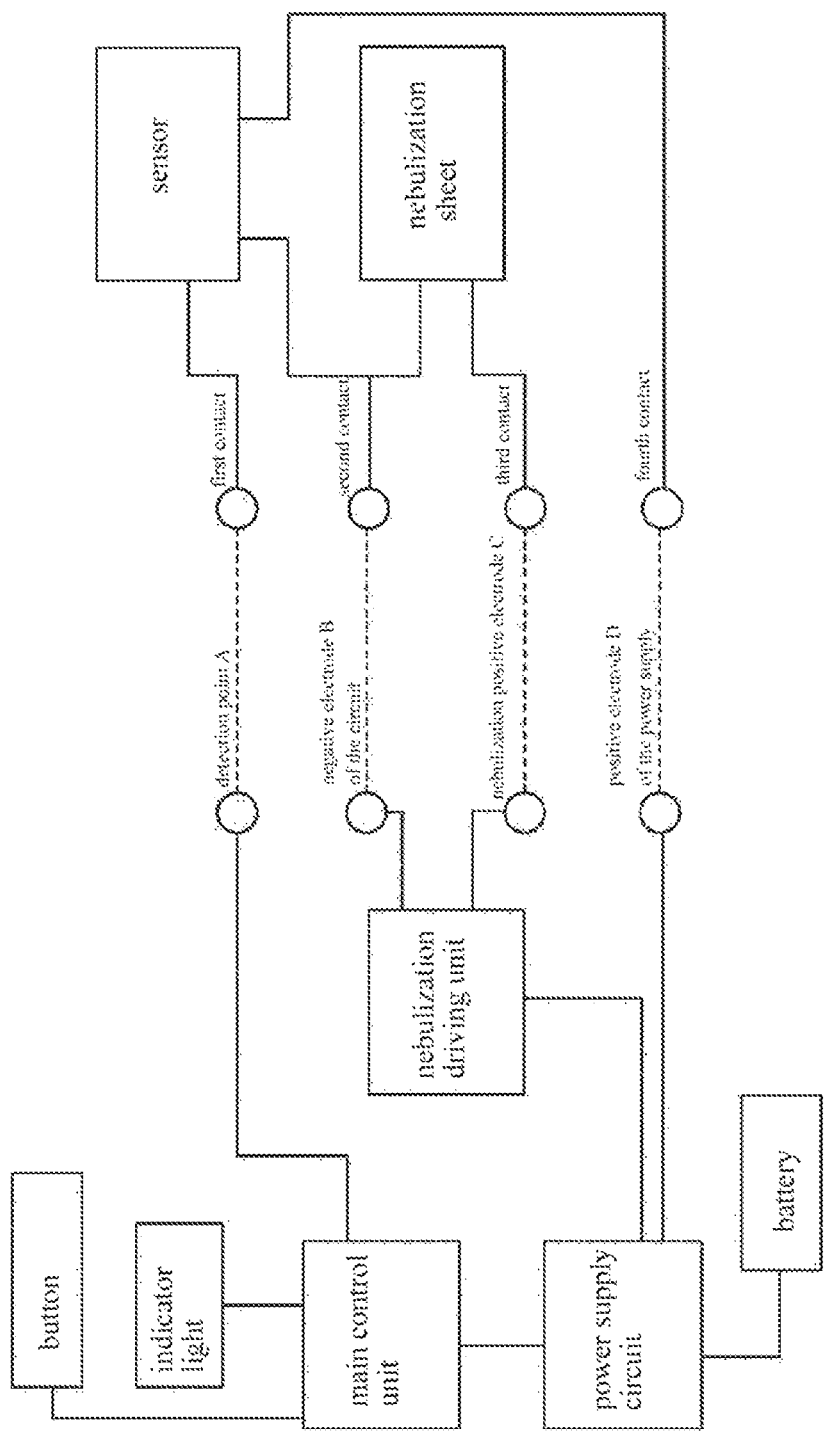
FIG. 6 is a schematic block diagram showing connection between the second circuit board and the first circuit board.
Figure 7:
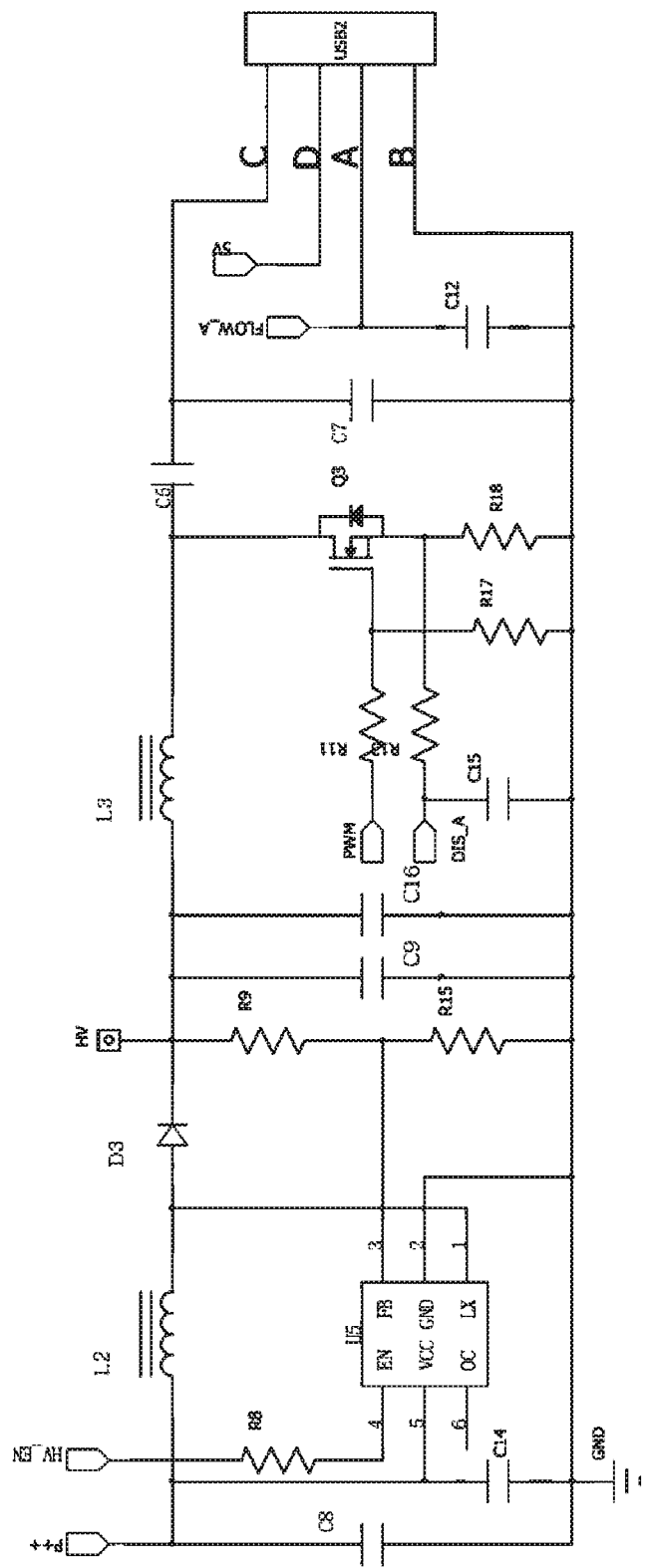
FIG. 7 is a circuit diagram of the second circuit board.

As shown in FIGS. 1-6, an ICU-special portable nebulization device enabling autonomous respiration according to airflow includes a nebulization control host 03, a nebulization generator 02 provided on the nebulization control host 03, and a tee connecting pipe 01 provided on the nebulization generator 02.

The nebulization generator 02 includes a bottom housing 21, a medicinal solution tank 22 provided on the bottom housing 21 and spaced apart from a space of the bottom housing 21, a medicinal solution outlet 23 provided on the bottom of the medicinal solution tank 22, an air guide port 24 provided on the bottom housing 21 at the same side as the medicinal solution outlet 23, a nozzle tube 25 sheathed on the periphery of the medicinal solution outlet 23 and the air guide port 24, a partition 26 provided in the nozzle tube 25 which separates the medicinal solution outlet 23 and the air guide port 24, a nebulization sheet 27 provided between the medicinal solution outlet 23 and the nozzle tube 25, and a first circuit board 28 provided in the bottom housing 21 which is connected with the nebulization sheet 27. The partition 26 in the nozzle tube 25 separates the interior of the nozzle tube 25 into a nebulization cavity 29 communicated with the medicinal solution outlet 23 and an air cavity 210 communicated with the air guide port 24. A sensor 211 connected with the first circuit board 28 is provided in the air cavity 210. The nozzle tube 25 on the side of the air cavity 210 is provided with a cross-section stopper 212 that blocks the opening of the air cavity 210. A first ventilation port 213 and a second ventilation port 214 communicated with the air cavity 210 are provided on two sides of the cross-section stopper 212, respectively. The first circuit board 28 extends to the outside of the bottom housing 21 and is connected with the nebulization generator 0202. The nebulization cavity 29 and the air cavity 210 are independent from each other, and the air cavity 210 will not affect the nebulization while detecting the state of the working airflow of the ventilator, so that the airflow detection and the nebulization spray do not interfere with each other. In addition, the sensor 211 is an air flow sensor 211 or an air pressure sensor.

The nebulization control host 03 includes a housing 31, a second circuit board 32 provided in the housing 31, and a button 33 and an indicator light 34 provided on the housing 31 which are connected with the second circuit board 32. The second circuit board 32 includes a main control unit, a power supply circuit connected with the main control unit, and a nebulization driving unit and a battery respectively connected with the power supply circuit. The button 33 and indicator light 34 are respectively connected with the main control unit. The second circuit board 32 is provided with four metal contacts in sequence, which are respectively a detection point A connected with the main control unit, a negative electrode B of the circuit and a nebulization positive electrode C respectively connected with the nebulization driving unit, and a positive electrode D of the power supply connected with the battery. The detection point A is connected with the sensor 211 and the main control unit, respectively, and is used to collect signal outputs of the sensor; the negative electrode B of the circuit is connected with the nebulization driving unit, the nebulization sheet 27 and the sensor 211, respectively, and is shared by the sensor 211 and the nebulization sheet 27; the nebulization positive electrode C is connected with the nebulization driving unit and the nebulization sheet 27, respectively to provide an alternating voltage required by the nebulization sheet 27 for operation; and the positive electrode D of the power supply is connected with the power supply circuit and the sensor 211, respectively to provide a direct voltage required by the sensor 211 for operation. The first circuit board 28 is provided with four metal contacts in sequence, which are a first contact conducted with the detection point A, a second contact conducted with the negative electrode B of the circuit, a third contact conducted with the nebulization positive electrode C, and a fourth contact conducted with the positive electrode D of the power supply. The first contact is connected with the sensor 211, the second contact is connected with the sensor 211 and the nebulization sheet 27, the third contact is connected with the nebulization sheet 27, and the fourth contact is connected with the sensor 211. The main control unit is connected with the sensor 211. The nebulization driving unit is connected with the nebulization sheet 27 for the purpose of detecting an air flow in the tee connecting pipe, sending a signal, and being controlled by the nebulization control host 03 to atomize the medicinal solution. Interfaces 35 are provided on the housing 31 at positions corresponding to the four metal contacts for facilitating conduction of the first circuit board 28 with the metal contacts of the second circuit board 32 after the first circuit board 28 is inserted. The power supply circuit includes a DC-AC conversion circuit and a booster circuit; and the nebulization sheet 27 and the sensor 21 use AC voltage and DC voltage, respectively. In addition, the power supply circuit may further include a charging circuit, a power switching circuit, and a battery, and is switched to an external power supply when an external AC voltage is connected. The nebulization control host 03 is provided with a clamp 04 for fixing the nebulization control host 03 to rails of a hospital bed or a table side. The clamp 04 includes a base 41, an inverted buckle 42 for fixing the nebulization control host 03 on the base 41, and a movable clip 43 for clamping the whole to the rails of the hospital bed or the table side. Left and right ends of the tee connecting pipe are respectively provided with a connecting pipe for connecting with an external piping of the ventilator and a face mask. The above connection may be implemented by interference fit connection to make the connection structure simpler. The left and right ends of the tee connecting pipe have different aperture sizes in order to distinguish the different ports connecting the ventilator and the face mask. It may be the case that one of the left and right ends of the tee connecting pipe with a larger aperture size is connected with the ventilator, and the end with a smaller aperture size is connected with the face mask. The tee connecting pipe is connected with the nozzle tube 25. A middle port of the tee connecting pipe is connected with the nebulization generator 0202, and the connection method thereof may also adopt interference fit connection. An inclined bottom surface 213 facing the medicinal solution outlet 23 is provided at the bottom, and an upper cover 212 is provided on the medicinal solution tank 22. The left and right ends of the tee connecting pipe 01 are respectively provided with the connecting pipe for connecting with the external piping of the ventilator and the face mask, and a middle pipe is communicated with the nebulization generator 02. The user can ventilate into the pipe. When the ventilator operates, an internal airflow change is detected and judged by the sensor 211 in the air cavity 210, and then the respiratory state of the ventilator is obtained. When the sensor 211 detects an air flow in the air cavity 210, the first circuit board 28 sends a signal to the nebulization control host 03, and then the nebulization control host 03 drives the nebulization driving unit to atomize the medicinal solution for drug delivery to the nebulization sheet 27 in the nozzle tube 25, so that not only the purpose of combining respiratory therapy and nebulization therapy is achieved, but also the therapeutic effect on the disease is better, avoiding the defect that the nebulization and the respiration are not synchronized. In addition, since the operation requirements on users are low during use, the present invention has the effects of simplicity and convenience. In addition, the nebulization generator 02 and the nebulization control host 03, as well as their connecting wires can be detachably connected, which is convenient for cleaning and replacing components such as the nebulization generator 02, and the product can be disassembled, which is convenient to carry, thereby realizing the effect of convenient use.

If the sensor 211 adopts an air pressure sensor, an air pressure can be detected. When the sensor 211 in the nebulization generator 02 detects that there is air flow, it sends a corresponding signal to the nebulization control host 03. If the main control unit reads a positive number, it represents a positive air pressure in the air cavity 210, which means that the ventilator is in an expiration state at this time, meanwhile the nebulization sheet 27 in the nebulization generator 02 is driven to atomize, and the atomized medicinal solution will enter the patient's mouth through the tee connecting pipe and the face mask together with the air supply of the ventilator. If the main control unit reads a negative number, it represents a negative air pressure in the air cavity 210, which means that the ventilator is in an inspiration state at this time, and the main control unit should control the nebulization generator 02 to stop nebulization of the nebulization sheet 27 at this time.

If the sensor 211 adopts an air flow sensor, an instantaneous flow rate and direction of the gas air can be detected. The positive or negative data read by the main control unit represent different flow directions of the air. For example, a positive number may represent that the air flows from the port of ventilator to the inside of the tee connecting pipe, that is, the ventilator is in the expiration state at this time; and a negative number may represent that the air flows from the inside of the tee connecting pipe to the port of ventilator, that is, the ventilator is in the inspiration state at this time, and whether the nebulization generator 02 sprays in different states is consistent with the air pressure sensor.

As shown in FIG. 7, U5 is a boost pressure 1C in a booster circuit of the power supply circuit. The DC voltage is converted into the AC voltage through an oscillation circuit composed of several inductors and capacitors in the circuit, and then boosted by a field effect transistor Q3, and finally led from point C to be used as the nebulization positive electrode to supply power to the nebulization sheet. Point D is connected with the DC voltage to serve as the positive electrode of the power supply to supply power to the sensor. Point A is the detection point for receiving the data of sensor, and is connected with a signal input pin of the main control unit for receiving data. Point B is the negative electrode of the circuit, which is shared by the sensor and the nebulization sheet as negative electrode and is connected with a ground wire.

What have been described above are only some embodiments of the present invention. For those of ordinary skill in the art, various modifications and improvements may be made without departing from the inventive concept of the present invention, which are all within the protection scope of the present invention.

The invention claimed is:

1. An ICU-special portable nebulization device enabling autonomous respiration according to airflow, comprising a nebulization control host, a nebulization generator provided on the nebulization control host, and a tee connecting pipe provided on the nebulization generator;

wherein the nebulization generator comprises a bottom housing, a medicinal solution tank provided on the bottom housing and spaced apart from a space of the bottom housing, a medicinal solution outlet provided on the bottom of the medicinal solution tank, an air guide port provided on the bottom housing at the same side as the medicinal solution outlet, a nozzle tube sheathed on the periphery of the medicinal solution outlet and the air guide port, a partition provided in the nozzle tube which separates the medicinal solution outlet and the air guide port, a nebulization sheet provided between the medicinal solution outlet and the nozzle tube, and a first circuit board provided in the bottom housing which is connected with the nebulization sheet;

wherein the partition in the nozzle tube separates the interior of the nozzle tube into a nebulization cavity communicated with the medicinal solution outlet and an air cavity communicated with the air guide port; a sensor connected with the first circuit board is provided in the air cavity;

wherein the nozzle tube on the side of the air cavity is provided with a cross-section stopper that blocks the opening of the air cavity, a first ventilation port and a second ventilation port communicated with the air cavity are respectively provided on two sides of the cross-section stopper; and wherein the first circuit board extends to the outside of the bottom housing and is connected with the nebulization generator.

2. The ICU-special portable nebulization device of claim 1, wherein the nebulization control host comprises a housing, a second circuit board provided in the housing, and a button and an indicator light provided on the housing which are connected with the first circuit board.

3. The ICU-special portable nebulization device of claim 2, wherein: the second circuit board comprises a main control unit, a power supply circuit connected with the main control unit, and a nebulization driving unit and a battery respectively connected with the power supply circuit;

the button and indicator light are respectively connected with the main control unit;

the second circuit board is provided with four metal contacts in sequence, which are respectively a detection point A connected with the main control unit, a negative electrode B of the circuit and a nebulization positive electrode C respectively connected with the nebulization driving unit, and a positive electrode D of the power supply connected with the battery.

4. The ICU-special portable nebulization device of claim 3, wherein: the first circuit board is provided with four metal contacts in sequence, which are respectively a first contact conducted with the detection point A, a second contact conducted with the negative electrode B of the circuit, a third contact conducted with the nebulization positive electrode C, and a fourth contact conducted with the positive electrode D of the power supply;

the first contact is connected with the sensor;

the second contact is connected with the sensor and the nebulization sheet; and the third contact is connected with the nebulization sheet;

the fourth contact is connected with the sensor; and the main control unit is electrically connected with the sensor, and the nebulization driving unit is connected with the nebulization sheet.

5. The ICU-special portable nebulization device of claim 3, wherein interfaces are provided on the housing at positions corresponding to the four metal contacts for facilitating conduction of the first circuit board with the metal contacts of the second circuit board after the first circuit board is inserted.

6. The ICU-special portable nebulization device of claim 3, wherein the power supply circuit comprises a DC-AC conversion circuit and a booster circuit; and the nebulization sheet and the sensor use an AC voltage and a DC voltage, respectively.

7. The ICU-special portable nebulization device of claim 1, wherein: the nebulization control host is provided with a clamp for fixing the nebulization control host to rails of a hospital bed or a table side;

the clamp comprises a base, an inverted buckle for fixing the nebulization control host on the base, and a movable clip that clamps the whole to the rails of the hospital bed or the table side.

8. The ICU-special portable nebulization device of claim 1, wherein left and right ends of the tee connecting pipe are respectively provided with connecting pipes for connecting with an external piping of the ventilator and a face mask.

9. The ICU-special portable nebulization device of claim 1, wherein the tee connecting pipe is connected with the nozzle tube.

10. The ICU-special portable nebulization device of claim 1, wherein: an inclined bottom surface facing the medicinal solution outlet is provided at the bottom; and an upper cover is provided on the medicinal solution tank.

11. The ICU-special portable nebulization device of claim 8, wherein the tee connecting pipe is connected with the nozzle tube.

* * * * *